United States Patent [19]

Shimura et al.

[11] Patent Number: 5,733,561
[45] Date of Patent: Mar. 31, 1998

[54] INSECTICIDE COMPOSITION AND PRODUCTION PROCESS THEREOF

[75] Inventors: Yoshinobu Shimura, Mobara; Tamotsu Asano, Chiba; Seiichi Shimono, Mobara; Takeshi Imakita, Chigasaki; Yukio Kiritani, Mobara; Yuuji Enomoto, Mobara; Toshio Matsumoto, Mobara, all of Japan

[73] Assignee: Mitsui Toatsu Chemicals, Incorporated, Tokyo, Japan

[21] Appl. No.: 357,971

[22] Filed: Dec. 16, 1994

Related U.S. Application Data

[63] Continuation of Ser. No. 971,779, filed as PCT/JP92/00701, May 29, 1992, published as WO92/22206, Dec. 23, 1992, abandoned.

[30] Foreign Application Priority Data

Jun. 12, 1991 [JP] Japan .................. 3-139935

[51] Int. Cl.$^6$ .................................... A01N 25/28
[52] U.S. Cl. .................. 424/408; 424/406; 424/405; 424/417; 424/419
[58] Field of Search .................. 424/489, 405, 424/501, 408; 264/4, 4.7, 5

[56] References Cited

U.S. PATENT DOCUMENTS

| | | | |
|---|---|---|---|
| 4,444,699 | 4/1984 | Hayford | 264/4.7 |
| 4,557,755 | 12/1985 | Takamashi et al. | 71/100 |
| 4,574,110 | 3/1986 | Asano et al. | 428/402.4 |
| 4,670,246 | 6/1987 | Dahl et al. | 424/419 |
| 4,956,129 | 9/1990 | Scher et al. | 264/4.7 |
| 5,051,306 | 9/1991 | Meinard et al. | 428/402.21 |
| 5,118,756 | 6/1992 | Asano et al. | 524/817 |
| 5,160,529 | 11/1992 | Scher et al. | 71/118 |

FOREIGN PATENT DOCUMENTS

| | | |
|---|---|---|
| 3629714 | 9/1986 | Germany . |
| 55-38325 | 10/1980 | Japan . |
| 61-11138 | 1/1986 | Japan . |
| 61-115006 | 6/1986 | Japan . |
| 63-178840 | 7/1988 | Japan . |
| 1-66104 | 3/1989 | Japan . |
| 64-66104 | 3/1989 | Japan . |
| 2-3602 | 1/1990 | Japan . |
| 2-196703 | 8/1990 | Japan . |
| 3-94826 | 4/1991 | Japan . |
| 2187957 | 3/1986 | United Kingdom . |

*Primary Examiner*—Neil S. Levy
*Attorney, Agent, or Firm*—Millen, White, Zelano, & Branigan, P.C.

[57] ABSTRACT

An aqueous suspension-type microcapsule insecticide composition which is obtained by emulsifying a hydrophobic admixture of liquid pyrethroid insecticide or a pyrethroid insecticide and a high boiling point solvent, preferably an alkyl ester of phthalic acid in which the alkyl group has 8–13 carbon atoms to form particles of a suitable size in the presence of an anionic water-soluble polymeric surface active agent and polycondensating melamine-formaldehyde or a derivative thereof on the surface of the said emulsified and dispersed particles, and a process for producing the composition. This composition exhibits stable insecticidal activity over a prolonged period with noticeably reduced toxicity to aquatic life.

8 Claims, No Drawings

INSECTICIDE COMPOSITION AND PRODUCTION PROCESS THEREOF

This application is a continuation of application Ser. No. 07/971,779, filed as PCT/JP92/00701, May 29, 1992, published as WO92/22206, Dec. 23, 1992, now abandoned.

TECHNICAL FIELD

This invention relates to a microcapsule insecticide composition and a production process thereof in which a melamine-formaldehyde or a derivative thereof in the presence of an anionic polymeric surface active agent encapsulates and covers a pyrethroid insecticide.

BACKGROUND OF THE INVENTION

Pyrethroid insecticides have generally been formulated as an emulsifiable concentrate by dissolving the insecticide in an organic Solvent mixed with a surface active agent or as an oily agent. In solid form, the insecticides have been formulated as a wettable powder in which the insecticide is adsorbed onto finely powdered mineral matter or diatomaceous earth, as a dust or as granule. However, these conventional formulations pose a variety of problems such as the pollution of the environment caused by the organic solvent used in the emulsions or by the dust resulting from the wettable powders. Furthermore, for these formulations to have long-term residual effectiveness, an amount much higher than that used in normal application is required, and this increased amount can affect the environment or cause problems of safety. There is therefore a strong demand for a formulation which maintains a high degree of efficacy over long periods.

Since many kinds of pyrethroid insecticides are highly toxic to fish, their use in paddy fields is restricted. Accordingly, there is a strong demand for a pyrethroid formulation which will be harmless to aquatic life when used in paddies.

Given this background, research and development are now actively under way to develop a superior microencapsulated formulation which in particular can effectively replace the emulsifiable concentrate or wettable powders and which will be much safer to use.

However, conventional microcapsules which encapsulate active insecticidal components are generally obtained through an interfacial polymerization reaction and are not ideal in terms of the production process or as an effective stabilized insecticide.

Microcapsules made by a complex coacervation method are not ideal in terms of the cost of the raw materials or in terms of storage stability. There is a need for a formulation which will resolve these problems, and which offers greater stability in terms of insecticidal activity.

Microcapsules in which a melamine-formaldehyde forms the wall film have been primarily developed for use in pressure-sensitive recording paper (Japanese Patent Laid-open No. 11138/1986). The technique for these microcapsules is disclosed as being primarily a pigment substance encapsulated within a covering, and in order to prevent color formation by the encapsulated substance without the application of pressure, the ratio by weight of core material to microcapsule wall film is adjusted to a range between 2:1–20:1, and the microcapsule particle size is limited to 5 micrometers or less.

Microcapsule formulations encapsulating pyrethroid insecticides have been disclosed, for example, a microencapsulated insecticide with a polyurethane as the covering (Japanese Patent Publication No. 38325/1980), a microencapsulated pyrethroid insecticide obtained by an interfacial polymerization reaction such as a polyamide, polyamide-polyurea, polyurethane, or polyurea (Japanese Patent Laid-open No. 115006/1986), a microencapsulated pyrethroid insecticide obtained by a complex coacervation method using gelatin-gum arabic (Japanese Patent Laid-open No. 66104/1989), and a microencapsulated insecticide with a polyurethane as the covering (Japanese Patent Laid-open No. 196703/1990).

In the microencapsulation process using the interfacial polymerization method (Japanese Patent Laid-open No. 115006/1986), one of the monomers undergoing polymerization must be dissolved in the core material. In cases where the monomer does not mix with the core material, microencapsulation is extremely difficult, and adequate insecticidal effectiveness cannot be obtained.

In the complex coacervation microencapsulation process using a type of natural polysaccharide (Japanese Patent Laid-open No. 66104/1989), the reaction can proceed under comparatively mild temperatures. However, there are a number of problems including the unstable supply of natural polysaccharides and the consequent possibility of large price fluctuations. Moreover, these microcapsules cannot be stored for prolonged periods as they are subject to putrefaction and coagulation, and accordingly, these products do not have adequate effectiveness as an insecticide.

Furthermore, microcapsules in which a melamine-formaldehyde forms the wall film have the problems that the applicable range of the ratio by weight of core material to microcapsule wall film or the microcapsule particle size prevents adequate insecticidal activity.

SUMMARY OF THE INVENTION

An object of this invention is to provide a pyrethroid insecticide microencapsulation composition in an aqueous suspension which has very little toxicity to aquatic creatures and which is stable over prolonged periods as an effective insecticide.

Another object of this invention was to produce a microcapsule insecticide composition in an aqueous suspension by using a hydrophobic liquid in which a liquid pyrethroid insecticide or a pyrethroid insecticide is dissolved or mixed with a core material solvent having a high boiling point, and a thin wall film formed from the polycondensation of one or more materials selected from the group consisting of a melamine-formaldehyde, a methylolmelamine monomer or a low molecular weight polymerization product thereof, an alkylated methylolmelamine monomer or a lower molecular weight polymerization product thereof, and a combination thereof.

In particular, the ratio by weight of core material to microcapsule wall film and the microcapsule particle size in these compositions have been adjusted to within an appropriate range, and the compositions therefore exhibit stable effectiveness as an insecticide over a very prolonged period compared with conventional formulations.

Moreover, these compositions are significantly less toxic to aquatic creatures in comparison with conventional pyrethroid emulsions or other insecticidal emulsions on the market.

The microcapsule insecticidal composition in aqueous suspension according to the present invention is produced by dissolving in water containing an anionic polymeric surface active agent one or more materials selected from the group consisting of a melamine-formaldehyde, a methylolmelamine monomer or a low molecular weight polymerization product thereof, an alkylated methylolmelamine monomer or a low molecular weight polymerization product thereof, and a combination thereof; adding to the said aqueous solution a liquid pyrethroid insecticide or a pyrethroid insecticide dissolved in a high boiling point solvent or mixed in a hydrophobic liquid; and emulsifying and heating the resultant mixture so that said melamine monomer and/or low molecular weight polymerization product thereof is allowed to polycondense around the said emulsified particles to form a wall film.

Examples of pyrethroid insecticides which can be used in this invention are listed below, but are not restricted to these compounds.

For example, 3-phenoxybenzyl(1RS)-cis, trans-3-(2,2-dichlorovinyl)-2,2-dimethylcyclopropane carboxylate [permethrin], α-cyano-3-phenoxybenzyl-1-(4-ethoxyphenyl)-2,2-dichlorocyclopropane carboxylate [cyloprothrin], (RS)-α-cyano-3-phenoxybenzyl(RS)-2-(4-chlorophenyl)-3-isovalerate [fenvalerate], (S)-α-cyano-3-phenoxybenzyl(S)-2-(4-chlorophenyl)isovalerate [esfenvalerate], α-cyano-3-phenoxybenzyl(S)-2-(4-difluoromethoxyphenyl)isovalerate [flucythrinate], α-cyano-3-phenoxybenzyl 2-(2-chloro-4-trifluoromethylaniline)isovalerate [fluvalinate], (RS)-α-cyano-3-phenoxybenzyl 2,2,3,3-tetramethylcyclopropane carboxylate [fenpropathrin], 3-phenoxybenzyl(1R)-cis, trans-chrysanthemate [d-fenothrin], (RS)-α-cyano-3-phenoxybenzyl(1R)-cis,trans-chrysanthemate [cyfenothrin], (RS)3-allyl-2-methyl-4-oxocyclopento-2-enyl(1RS)-cis, trans-chrysanthemate [allethrin], α-cyano-3-phenoxybenzyl(1R)-cis,trans-3-phenoxybenzyl(1R)-cis,trans-3-(2,2-dichlorovinyl)-2,2-dimethylcyclopropane carboxylate [cypermethrin], (S)-α-cyano-3-phenoxybenzyl(1R)-cis-3-(2,2-dibromovinyl)-2,2-dimethylcyclopropane carboxylate [deltamethrin], (S)-α-cyano-3-phenoxybenzyl(1R)-cis-2,2-dimethyl-3-(1,2,2,2-tetrabromoethyl)cyclopropane carboxylate [tralomethrin], 3,4,5,6-tetrahydro imidomethyl(1RS)-cis,trans-chrysanthemate [tetramethrin], 5-benzyl-3-furylmethyl(1RS)-cis,trans-chrysanthemate [resmethrin], α-cyano-4-fluoro-3-phenoxybenzyl(1R,trans)-2,2-dimethyl-3-(2,2-dichlorovinyl)cyclopropane carboxylate [cyfluthrin] can be used.

Of these, those chemicals and their isomers thereof which have the chemical structure as shown in general formula (1) below are preferred:

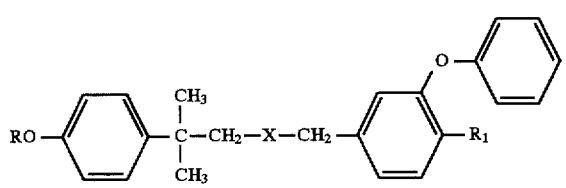

(1)

in which X is an oxygen atom or a methylene group, R is a lower alkyl group or a halomethyl group, $R_1$ is a hydrogen atom or a fluorine atom. Examples of chemical compounds of general formula (1) are as follows. The compound numbers will be referred to hereinafter.

Compound 1: 2-(4-ethoxyphenyl)-2-methylpropyl 3-phenoxybenzyl ether

Compound 2: 2-(4-difluorobromomethoxyphenyl)-2-methylpropyl 3-phenoxybenzyl ether Compound 3: 2-(4-ethoxyphenyl)-2-methyl-5-(4-fluoro-3-phenoxyphenyl)pentane Compound 4: 2-(4-difluorochloromethoxyphenyl)-2-methylpropyl 3-phenoxybenzyl ether Compound 5: 2-(4-trifluoromethoxyphenyl)-2-methylpropyl 3-phenoxybenzyl ether A mixture of any of these active insecticidal components or a mixture of other insecticides, acaricides, or similarly active ingredients can be used.

Preferably another high boiling point solvent can be blended as a cosolvent with these active insecticidal components within the core material. Substances which can be used as the high boiling point solvent include alkylbenzenes, phenylxylylethane, methylnaphthalene, or the various alkyl esters of phthalic acid, trimellitic acid, sebacic acid, adipic acid, or similar acids. In terms of stability, environmental effects, and other factors, the alkyl esters of phthalic acid, in which the alkyl radical has 8–13 carbon atoms are particularly preferred, and the alkyl radical can be either a straight chain or a branched chain. The proportion of cosolvent to be admixed is a function of the concentration of the active ingredients in the desired microcapsule, but a proportion of 10–90% of cosolvent in the hydrophobic solution, which is the core material, is preferred. Alkyl esters of phthalic acid having the alkyl radical of 8–13 carbon atoms according to the present invention include di-n-octyl phthalate, di-n-nonyl phthalate, di-isononyl phthalate, di-n-decyl phthalate, di-isodecyl phthalate, di-n-undecyl phthalate, di-n-dodecyl phthalate, and di-n-tridecyl phthalate. These phthalic acid alkyl esters can be used singly or as an admixture thereof. Moreover, if necessary, a synergist such as piperonyl butoxide, or other additive can be admixed into the core material.

Anionic polymeric surface active agents which can be used to emulsify and disperse the hydrophobic liquid core material can include a copolymer of ethylene and maleic anhydride, a copolymer of styrene and maleic acid, a copolymer of vinyl acetate and maleic anhydride or the like, an anionic polymeric surface active agent formed from the polymerization of at least one monomer selected from each of groups (A) acrylic acid or methacrylic acid, (B) acrylonitrile or methacrylonitrile, and (C) acrylamidoalkyl sulfonic acid or a sulfoalkyl ester of acrylic acid as disclosed in Japanese Patent Laid-open No. 4524/1986 is preferred. Moreover, a copolymerization product or salt thereof having a monomeric composition of 20–70 mole % of acrylic acid of group (A), 20–70 mole % of acrylonitrile of group (B) and 0.5–20 mole % of 2-acrylamido-2-methylpropane sulfonic acid of group (C) in which a 20% by weight aqueous solution of the said copolymerization product has a pH 4.0, and a viscosity of 10–1000 cps at 25° C., is preferred.

According to the present invention, the starting materials for the melamine-formaldehyde polycondensation product, which forms the wall film of the microcapsule of this invention, can be one or more water soluble capsule wall precursors selected from the group consisting of a melamine-formaldehyde, a methylolmelamine monomer or a low molecular weight polymerization product thereof, an alkylated methylol-melamine monomer or a low molecular weight polymerization product thereof, and a combination thereof.

As to the microencapsulation method, a melamine-formaldehyde or a derivative thereof, which is the capsule wall precursor, is dissolved in an aqueous solution of an anionic polymeric surface active agent, a hydrophobic solution containing the active insecticidal ingredient which becomes the core material is emulsified and dispersed into the resultant aqueous solution using a mixer for emulsification and dispersion, and the suspension thus obtained is then heated to induce the polymerization reaction.

The preferred method is to use an aqueous solution containing a specified amount of an anionic polymeric surface active agent of a type disclosed in the above Japanese Patent Laid-open No. 4524/1986, the pH of which is adjusted to about pH 4 using a 5N sodium hydroxide solution. A melamine-formaldehyde derivative used as the water soluble capsule wall precursor is then dissolved in the prepared aqueous solution, and using a mixer for emulsification and dispersion such as a T.K. Auto Mixer (a trade name, a product of Tokushu Kika Kogyo K.K.), a hydrophobic liquid, which contains the active insecticidal ingredient and which forms the core material, is emulsified and dispersed into the solution. The resultant disperse system is heated to approximately 60° C. and allowed to react for 2–3 hours to obtain the desired microcapsule slurry.

After encapsulation, the microcapsule suspension is diluted with water as required to produce a formulation of a specific insecticidal concentration, or if necessary, a suspension stabilizer is added to the formulation to form a stable slurry formulation.

To augment hygienic safety, after the microcapsule wall film is formed, the free formaldehyde remaining in the solution can be reduced or removed by the addition of urea, ethylene urea, sulfites, sugars, ammonia, amines, formamide, hydroxylamine salts (chloride, sulfate, phosphate), melamine, compounds having active methylene groups, hydroxyalkytamines, acrylamide, acrylamide copolymers, or other chemicals which will react with formaldehyde under suitable conditions to convert the residual formaldehyde into a harmless substance.

Substances which can be used as suspension stabilizers include natural polysaccharides such as xanthan gum and locust bean gum, semisynthetic polysaccharides such as carboxymethylcellulose and hydroxypropylcellulose, synthetic polymers such as sodium polyacrylate, and microfine mineral powders such as magnesium aluminum silicate and high-purity bentonite. These substances can be used singly or as an admixture of two or more of said substances. These substances stabilize the capsule slurry by increasing its viscosity.

In addition, in order to improve suspension stability or dispersion stability, anionic surface active agents such as lignin sulfonate, condensation product of sodium naphthalene sulfonate and formaldehyde, polyoxyethylene alkylaryl sulfates, polyoxyethylene styrylphenyl ether sulfate and polyoxyethylene nonyl ether sulfate, and nonionic surface active agents such as polyoxyethylene nonylphenyl ether, polyoxyethylene styrylphenyl ether, and polyoxyethylene alkylallyl ether can be admixed either singly or as a mixture of these substances.

The average particle size of the microcapsules to be prepared is a function of the type and concentration of the dispersing agent and the strength of mechanical agitation for emulsification and dispersion, but the average diameter of the microcapsules is normally in the range of 5–80 micrometers, and preferably 5–50 micrometers.

The ratio by weight of melamine-formaldehyde or derivative thereof to core material as used in the present invention is preferably between 1:500–1:20. The thickness of the microcapsule wall film will vary as a function of the ratio by volume of core material to the water soluble capsule wall precursor, but can be approximately determined from the following formula:

$$\text{Film thickness} = W_w/W_c \times p_c/p_w \times d/6$$

wherein d: average diameter of the microcapsules

Wc: weight of the core material

Ww: weight of the film substance

ρw: mass density of the wall substance

ρc: mass density of the core material

The film thickness of the microcapsules of this invention is between 10–500 nm. It is preferable to adjust the thickness to between 20–300 nm.

If the composition of this invention is to be used to prevent insect damage in paddy fields, vegetable farms, orchards, or the like, the composition can be diluted with water to a specific concentration for spraying. In this case, the insecticidal activity of this spray lasts a few weeks, a period several times longer than the effective period exhibited by conventional formulations such as emulsions with the same concentration of the active ingredients. Furthermore, even in comparison with other microcapsules having different types of wall films, the composition of this invention is superior in terms of both initial activity and residual effectiveness. Moreover, even in comparison with other microcapsules having the same type of wall film, because the weight of the wall film relative to the core material and the microcapsule particle size can be adjusted to the most appropriate range, the activity of this composition is superior not just in the short term, but over prolonged periods as well. In view of these points, in comparison with conventional formulations described previously, the insecticidal composition of the present invention is an extremely useful product given that it maintains its activity over prolonged periods and, since fewer sprayings are required, affords a reduction of energy consumption or a reduction of the amount of insecticide sprayed. Since the composition of this invention can reduce the high toxicity of synthetic pyrethroids to fish, it is also useful as a very safe formulation for the application of these pyrethroids to paddy fields.

Although the present invention will hereinafter be described in detail in the following Examples, Comparative Examples and Test Examples, it is to be understood that the invention is not limited to these examples.

EXAMPLE 1

An amount of 38.56 g of an anionic polymeric surface active agent (a 20% by weight aqueous solution of the copolymerization product of 60, 40, and 10 mole % of acrylic acid, acrylonitrile, and acrylmethylpropane sulfonic acid) was dissolved in 104.3 g of deionized water and the pH of the resultant solution was adjusted to approximately 4 using a 5N sodium hydroxide solution. 2.90 g (1.5% solid content relative to the core material) of U-RAMIN T-34 (a methylated methylolmelamine product manufactured by U-RAMIN Kogyo K.K.) was then added to the solution as the capsule wall precursor, and 154.24 g of a 50:50 mixture by weight of Compound 1 and Vinycizer-100 (an alkyl ester of phthalic acid in which the alkyl group has 10 carbon atoms, manufactured by Kao Corp.) was added as the core material, after which the solution was emulsified and dispersed at 5,000 rpm using a T.K. Auto Homo-Mixer (a trademark; manufactured by Tokushu Kika Kogyo K.K.). The emulsion was then heated while gently stirring for 2–3 hours in a constant temperature water bath at 60° C., from which a suspension of a microencapsulated product was obtained. Finally, a mixed solution of Kelzan S (xanthan gum manufactured by Sansho Seihin K.K.) and Jaguar-8111 (guar gum manufactured by Sansho Seihin K.K.) was added in the required amount to yield a final concentration of 0.05% of each substance. As a result, a microcapsule slurry of Compound 1 with an active ingredient concentration of 20% by weight and an average particle diameter of 30 micrometers was obtained.

EXAMPLE 2

The procedures of Example 1 were followed except that 154.24 g of a 50:50 admixed solution by weight of Compound 1 and Vinycizer-124 (an alkyl ester of phthalic acid in which the alkyl group has 10–12 carbon atoms, manufactured by Kao Corp.) was added as the core material, and a microcapsule slurry of Compound 1 with an active ingredient concentration of 20% by weight and an average particle diameter of 30 micrometers was obtained.

EXAMPLE 3

The procedures of Example 1 were followed except that 3.08 g of U-RAMIN T-34 (2.0% solid content relative to the core material) was added as the capsule wall precursor, and 154.24 g of a 50:50 by weight admixed solution of Compound 1 and DINP (an alkyl ester of phthalic acid in which the alkyl group has 9 carbon atoms, manufactured by Kyowa Hakko Kogyo Co., Ltd.) was added as the core material. A microcapsule slurry of Compound 1 with an active ingredient concentration of 20% by weight and an average particle diameter of 30 micrometers was obtained.

EXAMPLE 4

The procedures of Example 1 were followed except that 3.08 g of U-RAMIN T-34 was added as the capsule wall precursor, and 154.24 g of a 50:50 by weight admixed solution of Compound 1 and DnOP (an alkyl ester of phthalic acid in which the alkyl group has 8 carbon atoms, manufactured by Wako Pure Chemical Industries, Ltd.) was added as the core material. A microcapsule slurry of Compound 1 with an active ingredient concentration of 10% by weight was obtained.

EXAMPLE 5

The procedures of Example 1 were followed except that 3.08 g of U-RAMIN T-34 was added as the capsule wall precursor, 154.24 g of a 50:50 by weight admixed solution of Compound 1 and Vinycizer-100 was added as the core material, and the mixture was emulsified and dispersed at 7,000 rpm using a T.K. Auto Homo-Mixer. A microcapsule slurry of Compound 1 with an active ingredient concentration of 20% by weight and an average particle diameter of 20 micrometers was obtained.

EXAMPLE 6

The procedures of Example 5 were followed except that the speed of the T.K. Auto Homo-Mixer was set at 4,000 rpm, and a microcapsule slurry of Compound 1 with an active ingredient concentration of 20% by weight and an average particle diameter of 40 micrometers was obtained.

EXAMPLE 7

The procedures of Example 5 were followed except that the speed of the T.K. Auto Homo-Mixer was set at 8,000 rpm, and a microcapsule slurry of Compound 1 with an active ingredient concentration of 20% by weight and an average particle diameter of 15 micrometers was obtained.

EXAMPLE 8

The procedures of Example 1 were followed except that 2.90 g of U-RAMIN T-33 (a methylated methylolmelamine product manufactured by U-RAMIN Kogyo K.K.) was added as the capsule wall precursor, and a microcapsule slurry of Compound 1 with an active ingredient concentration of 20% by weight and an average particle diameter of 30 micrometers was obtained.

EXAMPLE 9

The procedures of Example 5 were followed except that 154.24 g of a 50:50 by weight admixed solution of Compound 3 and Hisol SAS-296 (phenylxylylethane, manufactured by Nippon Petrochemical Co., Ltd.) was added as the core material, and a microcapsule slurry of Compound 1 with an active ingredient concentration of 20% by weight and an average particle diameter of 20 micrometers was obtained.

EXAMPLE 10

The procedures of Example 5 were followed except that 154.24 g of a 50:50 by weight admixed solution of Compound 1 and Vinycizer-100 was added as the core material, and a microcapsule slurry of Compound 3 with an active ingredient concentration of 20% by weight and an average particle diameter of 20 micrometers was obtained.

EXAMPLE 11

The procedures of Example 5 were followed except that 154.24 g of a 40:60 by weight admixed solution of fenvalerate and Vinycizer-100 was added as the core material, and a microcapsule slurry of fenvalerate with an active ingredient concentration of 10% by weight and an average particle diameter of 20 micrometers was obtained.

EXAMPLE 12

The procedures of Example 5 were followed except that 154.24 g of a 30:70 by weight admixed solution of permethrin and Vinycizer-124 was added as the core material, and a microcapsule slurry of permethrin with an active ingredient concentration of 10% by weight and an average particle diameter of 20 micrometers was obtained.

EXAMPLE 13

The procedures of Example 1 were followed except that 0.77 g of U-RAMIN T-34 (0.5% of solids relative to the core material) was added as the capsule wall precursor, 154.24 g of a 25:75 by weight admixed solution of Compound 2 and Vinycizer-105 (an alkyl ester of phthalic acid in which the alkyl group has 10 carbon atoms, manufactured by Kao Corp.) was added as the core material, and the admixture was emulsified and dispersed at 9,000 rpm using a T.K. Auto Homo-Mixer. A microcapsule slurry of Compound 2 with an active ingredient concentration of 10% by weight and an average particle diameter of 10 micrometers was obtained.

EXAMPLE 14

The procedures of Example 13 were followed except that 1.54 g of U-RAMIN T-34 (1.0% of solids relative to the core material) was added as the capsule wall precursor, and a microcapsule slurry of Compound 2 with an active ingredient concentration of 10% by weight and an average particle diameter of 10 micrometers was obtained.

EXAMPLE 15

The procedures of Example 14 were followed except that the speed of the T.K. Auto Homo-Mixer was set at 10,000 rpm for emulsification and dispersion, and a microcapsule slurry of Compound 2 with an active ingredient concentration of 10% by weight and an average particle diameter of 5 micrometers was obtained.

EXAMPLE 16

The procedures of Example 14 were followed except that 77 g of an ethylene maleic anhydride copolymer was added as the anionic polymeric surface active agent, and a microcapsule slurry of Compound 2 with an active ingredient concentration of 5% by weight and an average particle diameter of 10 micrometers was obtained.

Comparative Example 1

An amount of 2.7 g of Olester-NP-2000 (hexamethylenedi-isocyanate, manufactured by Mitsui Toatsu Chemicals, Inc.) was dissolved in 100 g of a 50:50 by weight admixed solution of Compound 1 and Vinycizer-100, the entire batch of the composition thus obtained was added to 50 g of an aqueous solution of PVA-217 (polyvinyl alcohol, manufactured by Kureha Chemical Industry Co., Ltd.), and the resulting mixture was emulsified while stirring at 5,000 rpm using a T.K. Auto Homo-Mixer for several minutes. An amount of 0.25 g of hexamethylenediamine was then added, the pH of the resultant solution was adjusted to a minimum of 9, after which the mixture was allowed to react slowly at 50° C. for 2 hours whereby a microcapsule emulsion in which polyurea forms the wall film was obtained. Finally, a mixed solution of Kelzan S and Jaguar-8111 was added in the required amount to yield a final concentration of 0.05% of each substance, and a microcapsule slurry of Compound 1 with an active ingredient concentration of 20% by weight and an average particle diameter of 30 micrometers was obtained.

Comparative Example 2

The procedures of Comparative Example 1 were followed except that the speed of the T.K. Auto Homo-Mixer was set at 7,000 rpm for emulsification and dispersion, and a microcapsule slurry of Compound 1 with an active ingredient concentration of 20% by weight was obtained.

Comparative Example 3

An amount of 3.0 g of methylene di-isocyanate was dissolved in 100 g of a 50:50 by weight admixed solution of Compound 1 and Vinycizer-100, the entire batch of the composition thus obtained was added to 200 g of a 0.5% aqueous solution of PVA-217, the resultant mixture was emulsified while gently stirring at 5,000 rpm using a T.K. Auto Homo-Mixer for several minutes. Amounts of 4.5 g each of ethylenediamine and diethylenetriamine and 12.8 g of sodium carbonate were dissolved in 62 g of deionized water and the resultant aqueous solution was added to the emulsion. The mixture thus obtained was allowed to react slowly at 50° C. for 2 hours whereby a microcapsule emulsion in which a polyamide formed the wall film was obtained. Finally, a mixed solution of Kelzan S and Jaguar-8111 was added in the required amount to yield a final concentration of 0.05% of each substance, and a microcapsule slurry of Compound 1 with an active ingredient concentration of 20% by weight and an average particle diameter of 30 micrometers was obtained.

Comparative Example 4

The procedures of Comparative Example 3 were followed except that 1.5 g of methylene di-isocyanate was used and 4.3 g each of ethylenediamine and diethylenetriamine and 6.4 g of sodium carbonate were dissolved in 62 g of deionized water and added as an aqueous solution. A microcapsule slurry of Compound 1 with an active ingredient concentration of 20% by weight and an average particle diameter of 30 micrometers was obtained.

Comparative Example 5

The procedures of Example 1 were followed except that a 50:50 by weight admixed solution of Compound 1 and Vinycizer-100 was emulsified using PVA-217 (polyvinyl alcohol, manufactured by Kureha Chemical Industry Co., Ltd.), but no microcapsule slurry was obtained.

Comparative Example 6

The procedures of Example 5 were followed except that 12.34 g of U-RAMIN T-34 (8% solid content relative to the core material) was added as the capsule wall precursor, and 154.24 g of a 50:50 by weight admixed solution of Compound 1 and Vinycizer-100 was added as the core material. A microcapsule slurry of Compound 1 with an active ingredient concentration of 20% by weight and an average particle diameter of 20 micrometers was obtained.

Comparative Example 7

The procedures of Example 1 were followed except that 8.51 g of U-RAMIN T-34 (12% solid content relative to the core material) was added as the capsule wall precursor, and 54.24 g of a 50:50 by weight admixed solution of Compound 1 and Vinycizer-100 was added as the core material. A microcapsule slurry of Compound.1 with an active ingredient concentration of 20% by weight and an average particle diameter of 30 micrometers was obtained.

Comparative Example 8

The procedures of Example 13 were followed except that 15.42 g of U-RAMIN T-34 (10% solid content relative to the core material) was added as the capsule wall precursor, and 154.24 g of a 25:75 by weight admixed solution of Compound 2 and Vinycizer-105 was added as the core material. A microcapsule slurry of Compound 2 with an active ingredient concentration of 10% by weight and an average particle diameter of 10 micrometers was obtained.

Comparative Example 9

The procedures of Example 15 were followed except that 23.14 g of U-RAMIN T-34 (15% solid content relative to the core material) was added as the capsule wall precursor, and 154.24 g of a 25:75 by weight admixed solution of Compound 2 and Vinycizer-105 was added as the core material. A microcapsule slurry of Compound 2 with an active ingredient concentration of 10% by weight and an average particle diameter of 5 micrometers was obtained.

Comparative Example 10

The procedures of Example 13 were followed except that 154.24 g of a 50:50 by weight admixed solution of Compound 2 and dimethyl phthalate (an alkyl ester of phthalic acid in which the alkyl group has 1 carbon atom, manufactured by Wako Pure Chemical Industries, Ltd.) was added as the core material. A microcapsule slurry of Compound 2 with an active ingredient concentration of 10% by weight and an average particle diameter of 10 micrometers was obtained.

Comparative Example 11

The procedures of Example 13 were followed except that 154.24 g of a 50:50 by weight admixed solution of Compound 2 and dimethyl phthalate (an alkyl ester of phthalic acid in which the alkyl group has 2 carbon atoms, manufactured by Wako Pure Chemical Industries, Ltd.) was added as the core material. A microcapsule slurry of Compound 2 with an active ingredient concentration of 10% by weight and an average particle diameter of 10 micrometers was obtained.

Comparative Example 12

Trebon emulsion (20%) (commercially available, conventional formulation containing Compound 1).

Comparative Example 13

Ten parts by weight of Compound 2 and 4 parts by weight of Sorpol 355F (manufactured by Toho Chemical Industry Co., Ltd.) were dissolved in 86 parts by weight of mixed xylenes to obtain 100 parts by weight of an emulsion of Compound 2.

Comparative Example 14

Pydrin emulsion (30%) (foreign product: conventional formulation containing fenvalerate).

Comparative Example 15

Adion emulsion (20%) (commercially available, conventional formulation containing permethrin).

Comparative Examples 1, 2, 3, and 4 are examples of microencapsulated insecticide compositions corresponding to those of the present invention in which the components of the wall film differ from those according to the invention.

Comparative Example 5 is an example in which the polymeric surface active agent is nonionic.

Comparative Examples 6, 7, 8, and 9 are each an example in which the ratio by weight of the core material solution and the microcapsule wall film is not within the range of claim 6.

Comparative Examples 10 and 11 are each an example in which the number of carbon atoms in the alkyl group of the alkyl ester of phthalic acid in the core material is not within the range of claim 5.

Comparative Examples 12, 13, 14, and 15 are examples of conventional formulations which are emulsions of chemical compounds.

TEST EXAMPLES

Test Example 1

Tests were conducted to determine the insecticidal effectiveness of compositions obtained from Examples 1, 2, 3, 5, 8, 10, Comparative Examples 1, 4, 6, 7 and Comparative Example 12 against *Laodelphax atriatellus* Fallen (small brown planthopper). For the tests, 5 paddy-rice seedlings were bundled together, transplanted to a 1/10,000 are plastic pot, and allowed to grow inside a greenhouse for about 1–2 weeks until the plants reached the 4- or 5-leaf stage. Microencapsulated insecticidal compositions obtained from the Examples and Comparative Examples and Trebon emulsion of Comparative Example 10 were diluted with water so that the concentration of the active ingredient was 100 ppm, and the dilute solutions thus obtained were sprayed onto the paddy-rice plants. The pots were covered with wire mesh baskets, and 10 small brown planthoppers were released into each basket after each specified number of days, and the number of dead planthoppers were counted 24 hours after each release. Each test was repeated 3 times. Results are shown in Table 1.

TABLE 1

| | Proportion of Dead Planthoppers (%) Time of Insect Release into Pots | | | | |
|---|---|---|---|---|---|
| | Day 1 | Day 3 | Day 7 | Day 10 | Day 15 |
| Example 1 | 100.0 | 100.0 | 96.7 | 95.0 | 93.3 |
| Example 2 | 100.0 | 100.0 | 95.0 | 93.3 | 90.0 |
| Example 3 | 100.0 | 95.0 | 93.3 | 93.3 | 90.0 |
| Example 5 | 100.0 | 100.0 | 96.7 | 93.3 | 90.0 |
| Example 8 | 100.0 | 100.0 | 95.0 | 93.3 | 90.0 |
| Example 10 | 100.0 | 96.7 | 93.3 | 90.0 | 86.7 |
| Comparative Example 1 | 70.0 | 53.3 | 30.0 | 13.3 | 3.3 |
| Comparative Example 4 | 50.0 | 45.0 | 33.3 | 20.0 | 13.3 |
| Comparative Example 6 | 53.3 | 46.7 | 40.0 | 23.3 | 20.0 |
| Comparative Example 7 | 40.0 | 33.3 | 30.0 | 20.0 | 20.0 |
| Comparative Example 12 | 100.0 | 86.7 | 30.0 | 6.7 | 3.3 |

Day 1: The day of release.

Test Example 2

Tests were conducted to determine the insecticidal effectiveness of compositions obtained from Examples 13, 15, 16, and Comparative Examples 8, 9, 13 against *Tetranychus urticae* Koch (two-spotted spider mite). For the tests, microencapsulated insecticidal compositions of Compound 2 obtained from the Examples and Comparative Examples and an emulsion of Compound 2 obtained from Comparative Example 13 were diluted with water so that the concentration of the active ingredient was 25 ppm, and the dilute solutions thus obtained were sprayed onto kidney bean plants growing in pots in a greenhouse. At specified intervals in days, 2 cm square sections of leaves from each plant were excised, placed in a petri dish, and 10 two-spotted spider mites were released on top of the leaves.

The number of dead spider mites were counted 48 hours after each release. Each test was repeated two times. The results are shown in Table 2.

TABLE 2

| | Proportion of Dead Two-Spotted Spider Mites (%) Number of Days After Spraying | | | |
|---|---|---|---|---|
| | 1 Day | 7 Days | 14 Days | 25 Days |
| Example 13 | 100.0 | 90.0 | 90.0 | 90.0 |
| Example 15 | 100.0 | 95.0 | 90.0 | 90.0 |
| Example 16 | 100.0 | 90.0 | 85.0 | 80.0 |
| Comparative Example 8 | 40.0 | 35.0 | 30.0 | 20.0 |
| Comparative Example 9 | 30.0 | 30.0 | 30.0 | 20.0 |
| Comparative Example 13 | 100.0 | 90.0 | 40.0 | 10.0 |
| Untreated Block | 0.0 | 0.0 | 0.0 | 0.0 |

Test Example 3

Tests were conducted as to the toxicity to carp of the compositions obtained from Examples 11, 12, 13 and Comparative Example 11 and Comparative Examples 12 and 13. For the tests, each composition in an amount such that the final concentration of the active ingredient would be 5 ppm was added to 10 liters of dechlorinated tap water in a cylindrical glass water tank, and the mixture was stirred sufficiently to yield a homogeneous solution. Ten carp fry, each about 4–5 cm in length, were released into each water tank, and after 48 hours, the number of dead fish were determined. The results are shown in Table 3.

TABLE 3

| | Proportion of Dead Fish (%) |
|---|---|
| Example 11 | 0.0 |
| Example 12 | 0.0 |
| Example 13 | 0.0 |
| Comparative Example 11 | 100.0 |
| Comparative Example 12 | 100.0 |
| Comparative Example 13 | 100.0 |

The above results clearly reveal that the compositions of the present invention show a higher level of insecticidal activity over prolonged periods in comparison with conventional formulations, or other microcapsule compositions encapsulated with other types of wall films, and even those compositions using melamine derivatives in which the ratio by weight of the capsule-covering film to the core material exceeds the most appropriate range of the present invention, and that the toxicity of compositions according to the present invention to aquatic life is reduced considerably.

As explained above, the microencapsulated pyrethroid insecticide of the present invention in which a melamine-formaldehyde resin or derivative thereof forms the wall film exhibits a very stable level of activity over prolonged periods with greatly reduced toxicity to aquatic life. Furthermore, the active ingredients of the formulation are extremely effective in killing insects.

We claim:

1. An insecticidal composition comprising an aqueous suspension of microcapsules having a wall film encapsulating a core material, wherein the core material is a hydrophobic solution or suspension of a pyrethroid insecticide of formula (1)

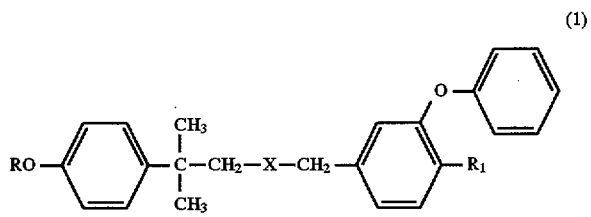

(1)

in which X is an oxygen atom or a methylene group, R is a lower alkyl group or a halomethyl group, and $R_1$ is a hydrogen atom, or a fluorine atom, in an alkyl ester of phthalic acid in which the alkyl group has 8–13 carbon atoms and the wall film is formed by the polycondensation, in water and in the presence of an anionic surface active agent, of one or more materials selected from the group consisting of a melamine-formaldehyde, methylolmelamine monomer or a polymerization product thereof, and an alkylated methylolmelamine or a polymerization product thereof, wherein the avionic surface active agent is a water-soluble anionic polymeric surface active agent obtained from the polymerization of an admixture of at least one monomer selected from each of the groups (A), (B) and (C), where (A) is acrylic acid or methacrylic acid, (B) is acrylonitrile or methacrylonitrile, and (C) is an acrylamidoalkylsulfonic acid or sulfoalkyl acrylate, and wherein the ratio by weight of core material to wall film is 500:1–20:1 and the average diameter of the microcapsules is 5–80 micrometers.

2. The insecticidal composition according to claim 1, wherein the pyrethroid insecticide is 2-(4-ethoxyphenyl)-2-methylpropyl 3-phenoxybenzyl ether.

3. The insecticidal composition according to claim 1, wherein the pyrethroid insecticide is 2-(4-difluorobromomethoxyphenyl)-2-methylpropyl 3-phenoxybenzyl ether.

4. The insecticidal composition of claim 1, wherein the core material further comprises piperonyl butoxide.

5. The insecticidal composition of claim 1, wherein the ionic surface active agent is a copolymerization product of a monomeric composition of (A) 20–70 mole % acrylic acid, (B) 20–70 mole % of acrylonitrile and 0.5–20 mole % of 2-acrylamido-2-methylpropane sulfonic acid or a salt thereof.

6. The insecticidal composition of claim 5, wherein the anionic surface active agent has a pH of 4.0 and a viscosity of 10–1000 cps at 25° C. in a 20% by weight aqueous solution.

7. The insecticidal composition of claim 1, wherein the wall film has a thickness of 16–500 nm.

8. The insecticidal composition of claim 1, wherein the wall film is formed by polycondensation of one or more materials selected from the group consisting of melamine-formaldehyde, methylolamine monomer and alkylated methylolamine.

* * * * *